(12) United States Patent
Hayakawa

(10) Patent No.: US 10,478,223 B2
(45) Date of Patent: Nov. 19, 2019

(54) ENDOSCOPIC TREATMENT TOOL

(71) Applicant: OLYMPUS CORPORATION, Hachioji-shi, Tokyo (JP)

(72) Inventor: Tomotaka Hayakawa, Kawaguchi (JP)

(73) Assignee: OLYMPUS CORPORATION, Tokyo (JP)

( * ) Notice: Subject to any disclaimer, the term of this patent is extended or adjusted under 35 U.S.C. 154(b) by 249 days.

(21) Appl. No.: 15/494,116

(22) Filed: Apr. 21, 2017

(65) Prior Publication Data

US 2017/0224380 A1 Aug. 10, 2017

Related U.S. Application Data

(63) Continuation of application No. PCT/JP2016/064315, filed on May 13, 2016.

(30) Foreign Application Priority Data

May 19, 2015 (JP) ................................. 2015-101766

(51) Int. Cl.
*A61B 17/221* (2006.01)
*A61B 17/22* (2006.01)
(Continued)

(52) U.S. Cl.
CPC ........ *A61B 17/50* (2013.01); *A61B 17/00234* (2013.01); *A61B 17/221* (2013.01);
(Continued)

(58) Field of Classification Search
CPC .. A61B 17/00234; A61B 17/221; A61B 17/50
See application file for complete search history.

(56) References Cited

U.S. PATENT DOCUMENTS 4,706,671 A * 11/1987 Weinrib ............... A61B 17/221
604/104
5,527,326 A 6/1996 Hermann et al.
(Continued)

FOREIGN PATENT DOCUMENTS

CN 103347453 A 10/2013
EP 2 638 870 A1 9/2013
(Continued)

OTHER PUBLICATIONS

Aug. 2, 2016 International Search Report issued in International Patent Application No. PCT/JP2016/064315.
(Continued)

*Primary Examiner* — Tuan V Nguyen
(74) *Attorney, Agent, or Firm* — Oliff PLC

(57) ABSTRACT

An endoscopic treatment tool according to the present invention including: a sheath an operating wire inserted into a sheath; a basket part positioned at a distal side of the operating wire, a distal end tip binding and fixing distal ends of the plurality of basket wires at a distal end of the basket part, a binding part in which proximal end portions of the plurality of basket wires are bound together and fixed, and a support member disposed so as to pass into the basket part along a central axis of the basket part and of which a distal end portion is fixed to the distal end tip. A proximal end portion of the support member is positioned at a proximal side than the binding part and is connected to the operating wire to be slidable in the central axis direction with respect to the operating wire.

15 Claims, 18 Drawing Sheets

(51) Int. Cl.
*A61B 17/50* (2006.01)
*A61B 17/00* (2006.01)

(52) U.S. Cl.
CPC ............... *A61B 2017/00314* (2013.01); *A61B 2017/00323* (2013.01); *A61B 2017/00818* (2013.01); *A61B 2017/2212* (2013.01)

(56) References Cited

U.S. PATENT DOCUMENTS

| | | |
|---|---|---|
| 2004/0122466 A1 | 6/2004 | Bales |
| 2014/0012283 A1* | 1/2014 | Yasuda ................ A61B 17/221 606/127 |

FOREIGN PATENT DOCUMENTS

| | | |
|---|---|---|
| JP | H06-133978 A | 5/1994 |
| JP | H06-296617 A | 10/1994 |
| JP | 2011-526188 A | 10/2011 |
| WO | 2009/158520 A1 | 12/2009 |
| WO | 2012/141213 A1 | 10/2012 |
| WO | 2015/087952 A1 | 6/2015 |

OTHER PUBLICATIONS

Dec. 14, 2018 Office Action issued in Chinese Patent Application No. 201680003581.1.

\* cited by examiner

ENDOSCOPIC TREATMENT TOOL

This application is a continuation application based on PCT Patent Application No. PCT/JP2016/064315, filed May 13, 2016, claiming priority claimed on Japanese Patent Application No. 2015-101766, filed on May 19, 2015, the contents of which are incorporated herein by reference.

BACKGROUND OF THE INVENTION

Field of the Invention

The present invention relates to an endoscopic treatment tool for collecting a foreign substance in a body.

Background Art

In the related art, endoscopic treatment tools, which are endoscopically inserted into a body and collect a foreign substance such as a calculus formed inside the body such as the bile duct, are known. For example, PCT International Publication No. 2012/141213 discloses an endoscopic treatment tool, which includes a basket part constituted a plurality of helical elastic wires and in which a calculus is collected by being accommodated inside the basket part. In the endoscopic treatment tool disclosed in PCT International Publication No. 2012/141213, in order to prevent overall of the basket part from being bent and collapsing, the basket part is provided with a support member. A distal end of the support member is fixed to a distal end of the basket part and the support member is disposed inside the basket part. A proximal end of the support member is disposed along a proximal portion of the basket part and is inserted into a flexible sheath.

When a large calculus is collected by an endoscopic treatment tool having such a basket part, for example, in regard to a relationship between the size of the basket part accommodating the calculus and the size of a lumen, there are cases where so called incarceration such that the basket part is caught inside the bile duct and disabling advance and retract inside the bile duct occurs. In a case where incarceration occurs, treatment of crushing (emergency crushing) a calculus inside the basket part is performed by a calculus crushing apparatus disclosed in Japanese Unexamined Patent Application, First Publication No. H6-133978. In the calculus crushing apparatus disclosed in Japanese Unexamined Patent Application, First Publication No. H6-133978, in a case where incarceration occurs, after a proximal end portion of an operating wire of the treatment tool exposed to the outside of the body is cut, an endoscope and the flexible sheath through which the treatment tool is inserted in a state where a calculus is accommodated inside the basket part are removed from the inside of the body. Next, a cut portion of the operating wire of the treatment tool is covered with a coil sheath of the calculus crushing apparatus, and the coil sheath is inserted into the body to reach a proximal end of the basket part. Thereafter, the cut portion of the operating wire is wound on a proximal end side of the coil sheath such that the basket part is taken into the coil sheath. Accordingly, wires of the basket part strongly tighten the calculus and crush the calculus. When the calculus is crumbled into small pieces through the crushing, the basket part becomes to be capable of removing from the inside of the bile duct.

SUMMARY OF THE INVENTION

According to a first aspect of the present invention, an endoscopic treatment tool including: a sheath; an operating wire inserted into the sheath to be capable of advancing and retracting; a basket part positioned at a distal side of the operating wire and formed by binding a plurality of elastic basket wires having helical shapes in a natural state; a distal end tip which binds and fixes distal ends of the plurality of basket wires at a distal end of the basket part; a binding part in which proximal end portions of the plurality of basket wires are bound together and fixed; and a support member disposed through the basket part along a central axis of the basket part, a proximal end portion of the support member being positioned inside the sheath, and a distal end portion of the support member being fixed to the distal end tip; and a connecting member positioned at a proximal side than the binding part, the connecting member connecting the proximal end portion of the support member with the operating wire inside the sheath such that the proximal end portion of the support member is along a longitudinal axis of the operating wire.

As a second aspect of the present invention, in the endoscopic treatment tool according to the first aspect, the binding part and a connecting part between the distal end tip and the distal ends of the plurality of basket wires may be positioned on the central axis, and the support member may be disposed at a position offset radially outward with respect to the central axis.

As a third aspect of the present invention, in the endoscopic treatment tool according to the second aspect, the connecting member includes a sliding part slidable with respect to the operating wire, and a holding part holding the proximal end portion of the support member at the position offset from the sliding part and along the central axis.

As a fourth aspect of the present invention, in the endoscopic treatment tool according to the third aspect, the connecting member may be formed of a pipe-shaped member. A through hole through which the operating wire is inserted and an insertion hole through which the support member is inserted may be formed side by side in the central axis direction.

As a fifth aspect of the present invention, in the endoscopic treatment tool according to the third aspect, the connecting member may have a loop part which is provided at a position extending from a proximal end of the support member and through which the operating wire is inserted.

As a sixth aspect of the present invention, in the endoscopic treatment tool according to the first aspect, the connecting member may be provided to be movable with respect to the sheath along the central axis.

As a seventh aspect of the present invention, in the endoscopic treatment tool according to the first aspect, the connecting member may be fixed to the proximal end portion of the supporting member or the operating wire. One of the proximal end portion of the supporting member and the operating wire may be connected to the connecting member so as to be slidable in the sheath along the central axis and slidable with respect to the other one of the proximal end portion of the supporting member and the operating wire.

As a eighth aspect of the present invention, in the endoscopic treatment tool according to the first aspect, the connecting member may be fixed to the proximal end portion of the supporting member, and may be connected to the operating wire so as to be slidable along the central axis with respect to the operating wire.

Effect of the Invention

According to the present invention, the endoscopic treatment tool is easily connected to a calculus crushing apparatus and emergency crushing is capable of performing favorably even in a case where incarceration occurs inside a lumen.

DESCRIPTION OF EMBODIMENTS

First Embodiment

Figure 1:
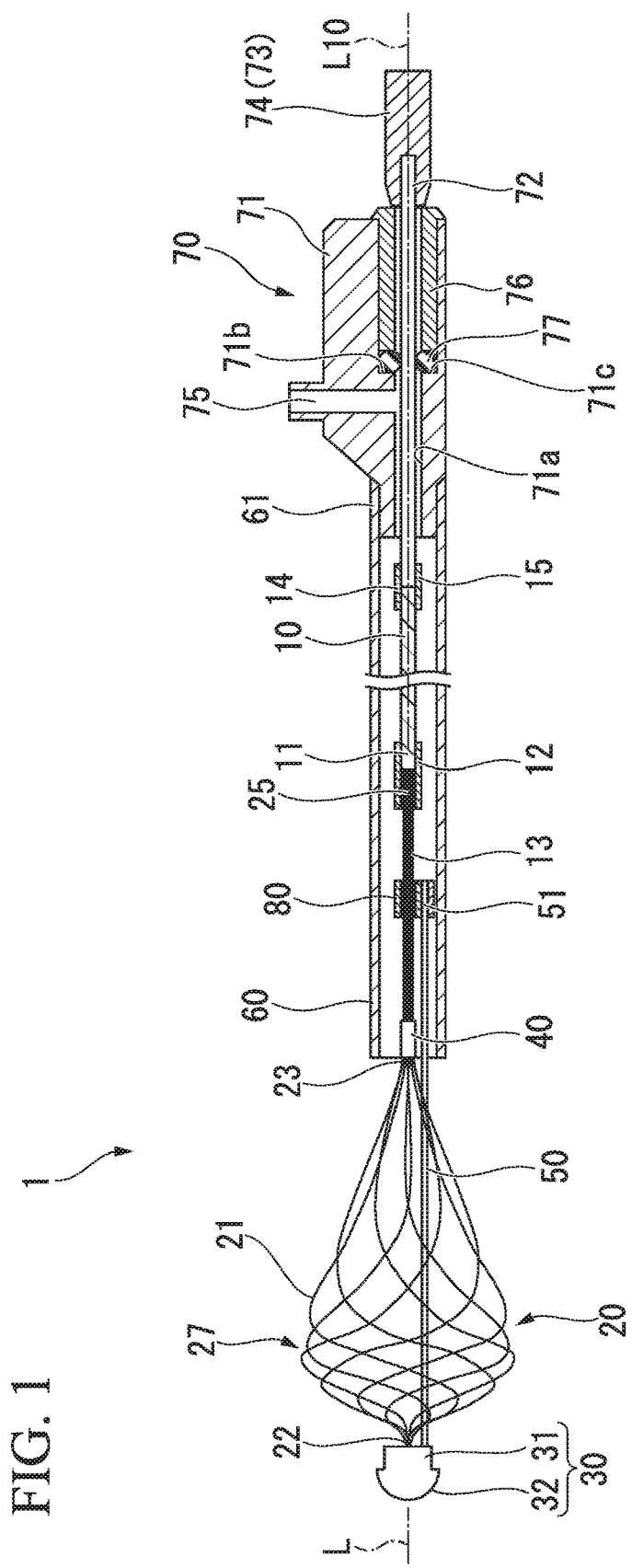
FIG. 1 is a cross-sectional view of an endoscopic treatment tool according to a first embodiment of the present invention.
Figure 2:
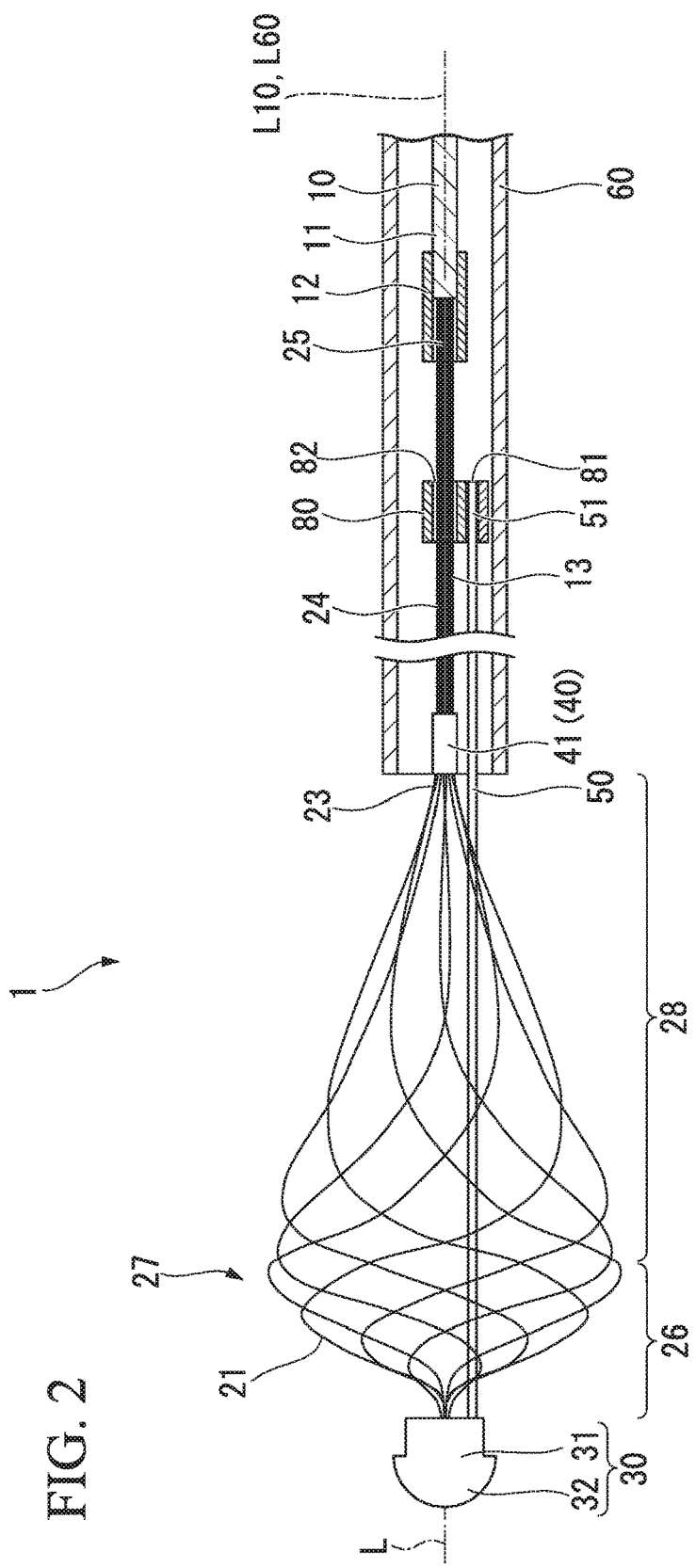
FIG. 2 is a partial cross-sectional view of a distal end portion of the endoscopic treatment tool according to the first embodiment of the present invention.

A treatment tool 1 for an endoscope (hereinafter, will be simply referred to as "treatment tool") according to a first embodiment of the present invention will be described. FIG. 1 is a cross-sectional view of the treatment tool 1. FIG. 2 is a partial cross-sectional view of a distal end portion of the treatment tool 1. The present embodiment will be described such that a side provided with an operating part 70 in a length direction of the treatment tool 1 is a proximal side, and a side opposite to the proximal side is a distal side.

As shown in FIG. 1, the treatment tool 1 has a configuration that an operating wire 10, a basket part 20, a distal end tip 30, a binding part 40, and a support member 50 are inserted to be capable of advancing and retracting through an inside of a flexible sheath (hereinafter, will be simply stated as "sheath") 60.

A proximal side of the operating wire 10 is connected to the operating part 70 and the operating wire 10 is inserted to be capable of advancing and retracting through the sheath 60. A distal end of the operating wire 10 is provided with the basket part 20. The operating wire 10 is subjected to an advance-retract operation with respect to the sheath 60 through an operation of the operating part 70 (will be described later). In the present embodiment, as the operating wire 10, a stranded wire formed of a plurality of metal wires is used.

The basket part 20 is positioned at the distal side of the operating wire 10 and is formed to have a basket shape in which a plurality of basket wires 21 are bound together. In the present embodiment, the basket part 20 is configured with eight basket wires 21. However, the number of basket wires 21 may be suitably set in consideration of easily collection of a calculus or suppressing drop off the calculus.

Each of the plurality of basket wires 21 is an elastic wire which has a helical shape in a natural state and is elastically deformable. The basket wire 21 is configured with a material having high elasticity, such as a solid wire and a stranded wire formed of a super-elastic alloy. For example, a nickeltitanium alloy, stainless steel, and a stainless alloy or the like are possible to be used as the material of the basket wire 21.

The basket wire 21 has a helical shape in its entirety in the length direction, and on the distal end side, the basket wire 21 is formed such that a helical pitch in an axial direction becomes short and the size in a radial direction (winding diameter of the helical) increases. Furthermore, on the proximal side of the basket wire, the helical shape becomes loosen compared to the distal side.

As shown in FIG. 1, in each of the basket wires 21, a distal end portion 22 is fixed to the distal end tip 30, and first proximal end portions (proximal end portions) 23, that is, portions configuring the basket part 20 are bound together with the binding part 40. Each of the basket wires 21 in a natural state has a shape helically wound around a central axis L connecting the distal end tip 30 and the binding part 40 and is configured to be elastically deformable. The central axis L of the basket part 20 is a line connecting a point where the distal ends of the basket wires 21 are bound together and fixed with the distal end tip 30, and the binding part 40 in which the first proximal end portions 23 of the basket wires 21 are bound together. The basket wires 21 have the same helical winding directions and the same wound shapes as each other. The basket wires 21 are disposed around the central axis L with equal interval and are bound together with the distal end portion 22 and at the first proximal end portions 23, thereby forming a basket. In the present embodiment, the basket wires 21 are wound counterclockwise when viewed from the distal end portion 22 in the direction of the first proximal end portion 23.

In the present embodiment, in the basket part 20, in a natural state where no external force is applied, as shown in FIGS. 1 and 2, a maximum diameter part 27 is formed on the distal end portion 22 side from an intermediate part of the basket part 20 in the length direction, and parts closer to the first proximal end portion 23 side than the maximum diameter part 27 is formed so as to have a loosen helical shape of which the pitch is greater than that of the maximum diameter part 27. The parts closer to the first proximal end portion 23 side than the maximum diameter part 27 functions as a collecting part 28 for collecting a foreign substance such as a calculus inside the basket part 20. In addition, parts closer to the distal end tip 30 side than the maximum diameter part 27 functions as a storage part 26 from which the foreign substance collected inside the basket part 20 is less likely to fall out of the basket part 20.

The distal end tip 30 is provided on a distal end side of the basket part 20, binds and fixes the distal end portions 22 of the basket wires 21 together. The distal end tip 30 has a tubular part 31 in which an insertion hole (not shown) is formed. The distal end portions 22 of the plurality of basket wires 21 are inserted into the insertion hole of the tubular part 31. Each of the distal end portions 22 of the basket wires 21 is fixed to the tubular part 31 through brazing, welding, caulking, resin welding, an adhesive or a combination thereof. The distal end side of the tubular part 31 is provided with a substantially hemispherical protective part 32 having a radius greater than that of the tubular part 31. The protective part 32 is provided for the purpose of preventing the distal end portions 22 of the basket wires 21 from pricking biological tissue or being caught by biological tissue when the treatment tool 1 is used such that the basket part 20 is smoothly inserted. A distal end portion of the support member 50 (will be described later) is inserted and fixed to the tubular part 31 of the distal end tip 30.

The binding part 40 is a portion in which the first proximal end portions 23 of the plurality of basket wires 21 are bound together and fixed. As the binding part 40, a configuration in which the basket wires 21 are fixed to each other through brazing, welding, caulking, resin welding, an adhesive or a combination thereof, or a configuration in which the outer circumferential side of the plurality of basket wires 21 is surrounded by a binding member and is fixed is possible to be used. In the present embodiment, the binding part 40 is configured that each of the basket wires 21 is inserted through the tubular binding member 41 and is fixed.

As shown in FIG. 2, each of the plurality of basket wires 21 includes a straight part 24, which have a linear shape in a natural state, on the proximal side from the binding part 40, that is, on more proximal side than the first proximal end portions 23.

The straight parts 24 of the basket wires 21 are extended in an axis direction of the operating wire 10 while being bound together without fixing each other. Proximal ends 25 of the straight parts are connected to a distal end portion 11 of the operating wire 10. The distal end portion 11 of the operating wire 10 and the proximal ends 25 of the basket wire 21 are individually inserted through the inside of a substantially tubular first coupling part 12 and are fixed. Each of the straight parts 24 of the basket wires 21 does not configure the basket part 20 and functions as a second operating wire part (operating wire) 13 which advances and retracts while following the advance-retract operation of the operating wire 10. That is, in the basket wire 21, a portion from the distal end portion 22 to the first proximal end portion 23 configures the basket part 20, and the straight part 24 on the proximal side from the binding part 40 configures the second operating wire part 13.

The support member 50 is an elastic wire having rigidity higher than that of the basket wire 21. As shown in FIGS. 1 and 2, the support member 50 is disposed so as to pass through the inside of the basket part 20 along the central axis L of the basket part 20. As shown in FIG. 2, the central axis L of the basket part 20 is positioned to be substantially coaxial with the central axis L10 of the operating wire 10. The distal end of the support member 50 is fixed to the tubular part 31 of the distal end tip 30. A length of the support member 50 is set such that the proximal end of the support member 50 is positioned inside the sheath 60 even in a state where the basket part 20 maximally protrudes from the distal end of the sheath 60. The support member 50 is disposed such that the central axis of the support member does not coincide with the central axes of the basket part 20 and the distal end tip 30 and is substantially parallel to the central axis L of the basket part 20. That is, the support member 50 is fixed to the tubular part 31 outside in the radial direction from a fixing part of the plurality of basket wires 21 in the tubular part 31, and the support member 50 is held at a position offset with respect to the central axis L of the basket part 20. The support member 50 supports the basket part 20 such that a state where the distal end tip 30 is positioned on the central axis L of the basket part 20 is maintained. The support member 50 has rigidity with a level that the support member 50 is capable of being bent while following a bending operation such as bending of the sheath 60 when being accommodated in the sheath 60.

A proximal end portion 51 of the support member 50 is disposed at the proximal side from the binding part 40. The proximal end portion 51 is connected to the operating wire 10 at a position where is the proximal side than the binding part 40 and the proximal end portion 51 is slidable with respect to the operating wire 10 in a direction of the central axis L10. Specifically, the proximal end portion 51 of the support member 50 is connected to the operating wire 10 via a connecting member 80. The support member 50 is not fixed to the second operating wire part 13 and the operating wire 10. The support member 50 advances and retracts inside a lumen of the sheath 60 in a longitudinal direction of the sheath 60 independently from the basket wires 21 and the operating wire 10.

As shown in FIG. 2, the connecting member 80 is a substantially tubular member. An insertion hole 81 in which the support member 50 is inserted and a through hole 82 through which the second operating wire part 13 is inserted are formed in the connecting member 80. The insertion hole 81 and the through hole 82 extend in a direction of the central axis L of the basket part 20. The insertion hole 81 and the through hole 82 are formed side by side and are parallel to each other. The through hole 82 has an opening diameter greater than the outer diameter of a bundle of the plurality of basket wires 21 configuring the second operating wire part 13, and the second operating wire part 13 is inserted through the through hole 82 to be capable of advancing and retracting. The proximal end portion 51 of the support member 50 is inserted through the insertion hole 81 and is fixed through brazing, welding, caulking, resin welding, an adhesive or a combination thereof. When the support member 50 and the operating wire are respectively inserted through the insertion hole 81 and the through hole 82, the support member 50 is positioned along the operating wire 10 at the proximal side than the binding part 40, and the support member 50 and the operating wire 10 is capable of maintaining a separation distance therebetween.

Figure 5:
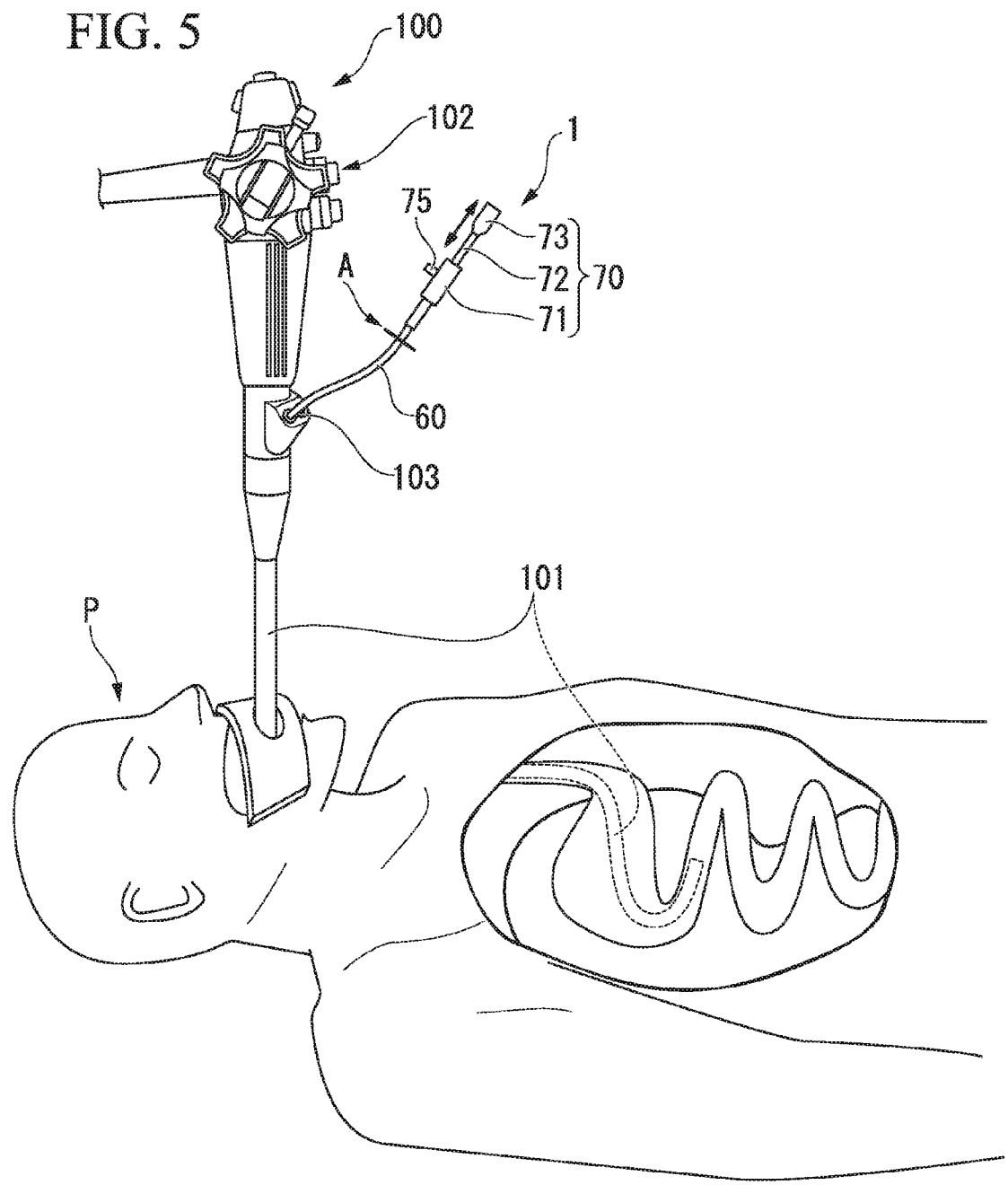
FIG. 5 is a view showing an aspect of using the endoscopic treatment tool according to the first embodiment of the present invention.

The sheath 60 is inserted into an endoscope insertion part 101 (FIG. 5). The sheath 60 can be configured by suitably selecting or combining a coil sheath formed by winding a known resin material such as a fluororesin and a thermoplastic elastomer, or a metal wire; a braid in which a metal wire is used; and the like. The central axis L of the basket part 20 is at least positioned to be parallel to the central axis L60 of the sheath 60. More preferably, the central axis L of the basket part 20 is positioned on the central axis L60 of the sheath 60.

As shown in FIG. 1, the operating part 70 is provided at the proximal end portion of the treatment tool 1. The operating part 70 has an operating body 71, a shaft 72, and a slider 73. The operating body 71 is provided at the proximal side of the sheath 60. Inside the operating body 71, A through path 71a extending the sheath 60 in the axis direction is formed. The operating body 71 is connected to a proximal end portion 61 of the sheath 60 such that the through path 71a communicates with the inside of the sheath 60. The shaft 72 is inserted through the penetration path 71a, and a distal end of the shaft 72 is connected to a proximal end 14 of the operating wire 10 via a second coupling part 15. The proximal end of the shaft 72 protrudes from the proximal side of the through path 71a and is fixed to the slider 73. The slider 73 has a gripping part 74 which is capable of gripping by an operator. The shaft 72 is provided to be capable of advancing and retracting inside the through path 71a with respect to the operating body 71.

The operating body 71 further includes a liquid supply port 75. The liquid supply port 75 is formed to communicate with the through path 71a. For example, the liquid supply port 75 is configured to be capable of being connected to a known syringe or pump. The through path 71a has an opening diameter that liquid is capable of being supplied in a state where the shaft 72 is inserted therethrough. An increased diameter part 71b further increased in diameter than the distal side is formed in the through path 71a at the proximal side than the liquid supply port 75. A step part 71c is formed between the increased diameter part 71b and the proximal side of the through path 71a. A fitting member 76 tubularly formed along a shape of an inner circumferential face of the increased diameter part 71b is inserted from the proximal end side of the operating body 71 and is fitted into the increased diameter part 71b. An O-ring 77 is externally mounted onto the outer circumference of the shaft 72, and the O-ring 77 is disposed between the fitting member 76 and the step part 71c. Due to such a configuration, the proximal side of the through path 71a is maintained in water-tightly state. Therefore, in a case where liquid supply is performed through the liquid supply port 75 which communicates with the through path 71a, a fluid is capable of being prevented from leaking to the proximal side (increased diameter part 71b side) than the liquid supply port 75 of the through path 71a.

Figure 3:
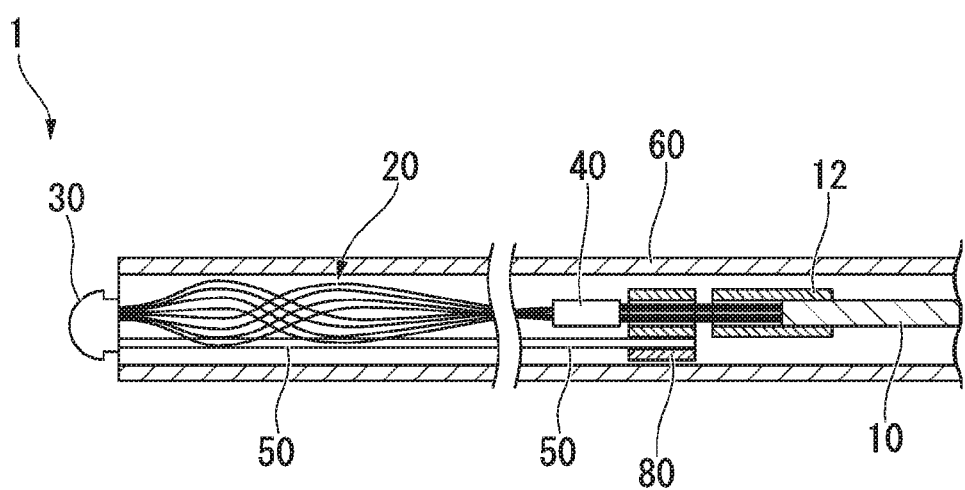
FIG. 3 is a partial cross-sectional view of the distal end portion of the endoscopic treatment tool according to the first embodiment of the present invention.
Figure 4:
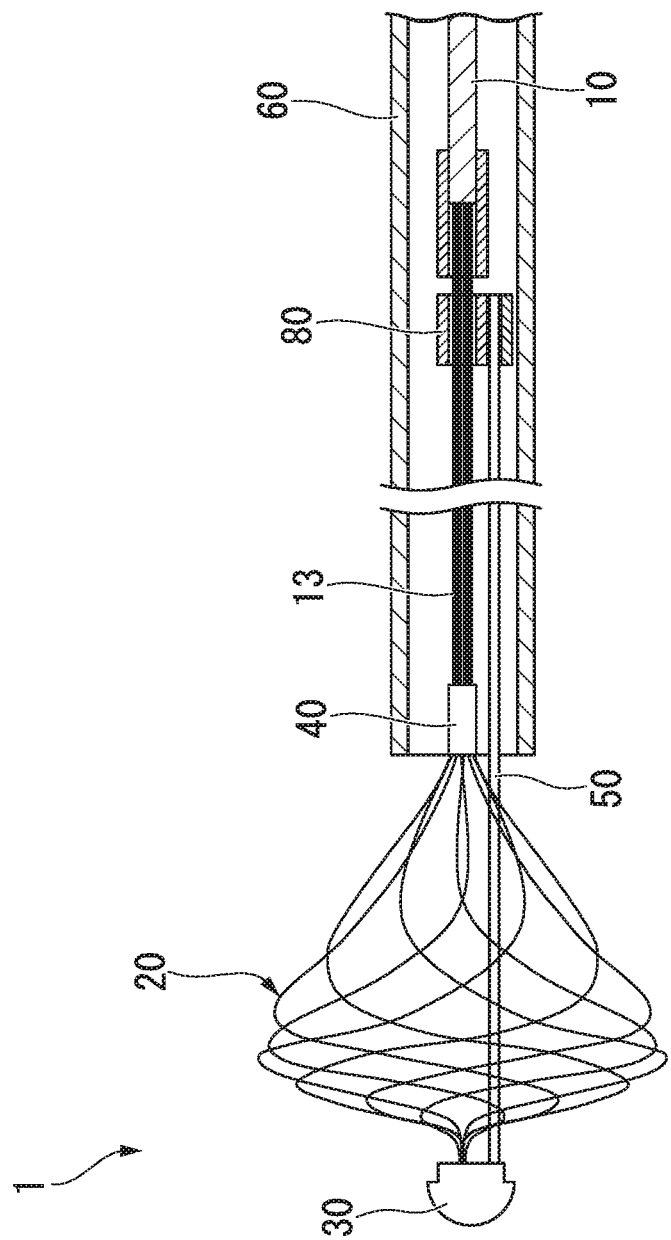
FIG. 4 is a partial cross-sectional view of the distal end portion of the endoscopic treatment tool according to the first embodiment of the present invention.

An operation of the treatment tool 1 configured as described above will be described with reference to FIGS. 2 to 4. FIGS. 3 and 4 are cross-sectional views showing the distal end portion of the treatment tool 1.

FIG. 2 is a view showing a state where the basket part 20 is pushed out from the distal end of the sheath 60. In a state where the basket part 20 is pushed out from the distal end of the sheath 60 and no external force is applied to the basket part 20, the basket part 20 forms a basket in a basic shape applied in advance as shown in FIG. 2, due to restoring forces of the basket wires 21. In this case, the proximal end portion 51 of the support member 50 is connected to the second operating wire part 13 through the connecting member 80 inside the lumen of the sheath 60 at a substantially intermediate position of the second operating wire part 13 (intermediate position between the binding part 40 and the first coupling part 12).

Since the basket part 20 is configured with the helical basket wires 21 as described, when the basket part 20 protrudes from the sheath 60, a basket shape is formed such that a foreign substance is easily captured and can be easily held. Moreover, when the basket part 20 is taken into the sheath 60, the basket part 20 is smoothly reduced in diameter and is easily accommodated in the sheath 60. At the time of the advance-retract operation of the basket part 20 with respect to the sheath 60, the support member 50 is capable of supporting the basket part 20 while maintaining the central axis L of the basket part 20 to be parallel to the central axis L60 of the sheath 60.

FIG. 3 shows a state where the basket part 20 is accommodated in the sheath 60. In a state where the basket part 20 is accommodated in the sheath 60, the basket part 20 is elastically deformed by being pressed by an inner wall of the lumen of the sheath 60, and is thereby further reduced in diameter than the basic shape shown in FIG. 2. When the basket part 20 is reduced in diameter, the overall length of the basket part 20 relatively extends in a direction of the central axis L, and the distal end tip 30 moves in a direction of being separated with respect to the binding part 40. In accordance with a movement of the distal end tip 30 in the direction of being separated from the binding part 40, the support member 50 is pulled to the distal end side, and a length of a portion disposed inside the basket part 20 increases.

In this case, since the proximal end portion 51 of the support member 50 is fixed to the connecting member 80, the connecting member 80 relatively moves to the distal side in the through hole 82 with respect to the second operating wire part 13 and approaches the binding part 40. That is, the proximal end portion 51 of the support member 50 moves to the distal end side in accordance with a reduction in diameter of the basket part 20, while maintaining a state of being positioned along the second operating wire part 13 and a state of being side by side in a parallel manner. In this case, the support member 50 maintains a state where the distal end tip 30 is positioned on the central axis L of the basket part 20 and functions as a core material supporting the basket part 20. Therefore, the plurality of basket wires 21 are accommodated in the sheath 60 in a state of being elastically deformed in a substantially linear manner along the support member 50.

FIG. 4 is a view showing a state where the overall length of the basket part 20 becomes shorter than that of the basic shape in FIG. 2 due to an external force applied to the basket part 20 in a state where the basket part 20 protrudes from the distal end of the sheath 60. For example, when the operating wire 10 is pulled toward the proximal side in a state where the treatment tool 1 is inserted into the lumen, in a case where a pressing force toward the proximal side by the limen tissue acts on the distal side than the maximum diameter part 27 of the basket part 20, the basket part 20 may have such a shape. In a case where the basket part 20 is in a state shown in FIG. 4, the distal end tip 30 moves to a position closer to the binding part 40 than that at the time of the basic shape. In this case, the support member 50 is applied a force to be pushed toward the proximal direction, and the proximal end portion 51 of the support member 50 approaches the first coupling part 12. Since the proximal end portion 51 of the support member 50 is fixed to the connecting member 80, in the through hole 82, the connecting member 80 relatively moves toward the proximal side with respect to the second operating wire part 13 and approaches the second coupling part 15. That is, the proximal end portion 51 of the support member 50 moves toward the proximal side in accordance with a reduction in overall length of the basket part 20 while maintaining a state being positioned along the second operating wire part 13 and a state of being side by side in a parallel manner.

In a case shown in FIG. 4, the support member 50 maintains a state where the distal end tip 30 is positioned on the central axis L of the basket part 20 and functions as a core material supporting the basket part 20. Therefore, the basket part 20 maintains a state where the distal end tip 30 is positioned on the central axis L by the support member 50, and a state where a space is formed inside the basket part 20 is maintained.

Next, a procedure in which the treatment tool 1 is used will be described. Hereinafter, description will be given while exemplifying a procedure of removing a foreign substance such as a calculus formed inside a bile duct BD. FIGS. 5 to 11 are views showing an aspect of using the treatment tool 1 and an endoscope apparatus 100. As shown in FIG. 5, the treatment tool 1 according to the present embodiment is used by being inserted into the endoscope insertion part 101 of the endoscope apparatus 100.

Figure 6:
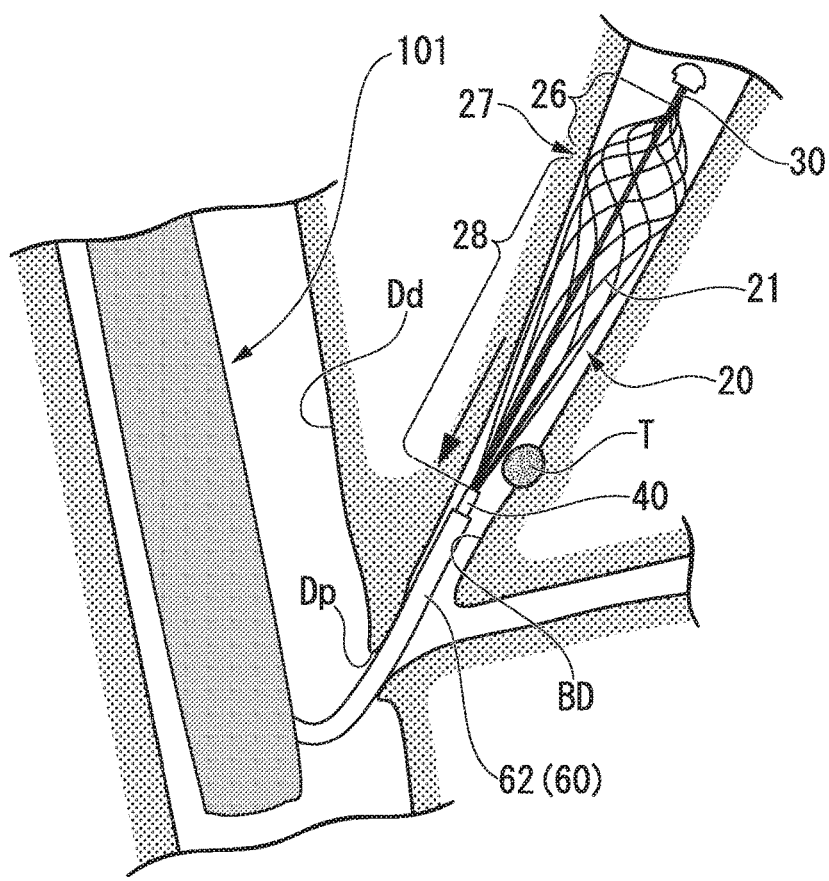
FIG. 6 is a view showing the aspect of using the endoscopic treatment tool according to the first embodiment of the present invention.

First, as shown in FIG. 5, the operator inserts the endoscope insertion part 101 of the endoscope apparatus 100 into a digestive tract from the mouth, for example. As shown in FIG. 6, the operator inserts the distal end of the endoscope insertion part 101 to a duodenum Dd while observing the circumstances with imaging means (not shown). Subsequently, the operator inserts the treatment tool 1 into the endoscope insertion part 101 of the endoscope apparatus 100 through an insertion port 103 (refer to FIG. 5). As shown in FIG. 6, the operator causes a distal end part 62 of the sheath 60 to protrude from the distal end of the endoscope insertion part 101. When the distal end part 62 of the sheath 60 is caused to protrude, the sheath 60 is raised by using an elevator (not shown) provided inside the endoscope insertion part 101 by operating an endoscope operating part 102 of the endoscope apparatus 100. The operator causes the sheath 60 to advance with respect to the endoscope insertion part 101 and to enter the inside of the bile duct BD, and the sheath 60 is inserted until the distal end part 62 reaches at a location in the vicinity of a calculus T generated inside the bile duct BD.

Subsequently, the operator grips the gripping part 74 and thrusts the slider 73 toward the distal side, thereby the basket part 20 is protruded from the distal end part 62 of the sheath 60. When the slider 73 is thrust until the slider 73 abuts on the proximal end portion of the operating body 71, the binding part 40 protrudes from the distal end part 62 of the sheath 60. In this case, as shown in FIG. 6, the calculus T is positioned at the proximal side than the maximum diameter part 27 of the basket part 20.

Subsequently, the operator pulls the slider 73 toward the proximal side and causes the basket part 20 to retract into the distal end part 62 of the sheath 60. In the basket part 20, the separation distances among the basket wires 21 are wide in the collecting part 28 at the proximal side than the maximum diameter part 27. Therefore, when the basket part 20 is taken into the proximal side in a state where the calculus T abuts on the basket wires 21 of the collecting part 28, the basket wires 21 of the collecting part 28 are pushed to be widened by the calculus T, and the calculus T is thereby collected inside the basket part 20. When the calculus T is collected inside the basket part 20, the operator further moves the slider 73 toward the proximal side and causes the collecting part 28 to be accommodated in the sheath 60. In this case, the calculus T is held by the plurality of basket wires 21 in a state of being accommodated in the storage part 26 of the basket part 20. Subsequently, the operator causes the endoscope insertion part 101 to retract to discharge the basket part 20 to the outside of the body and the calculus T is discharged to the outside of the body, thereby collecting the calculus T.

When steps of a procedure described above are performed, the support member 50 advances and retracts along the second operating wire part 13 by the connecting member 80. The basket part 20 is supported by the support member 50 while keeping an internal space.

Figure 7:
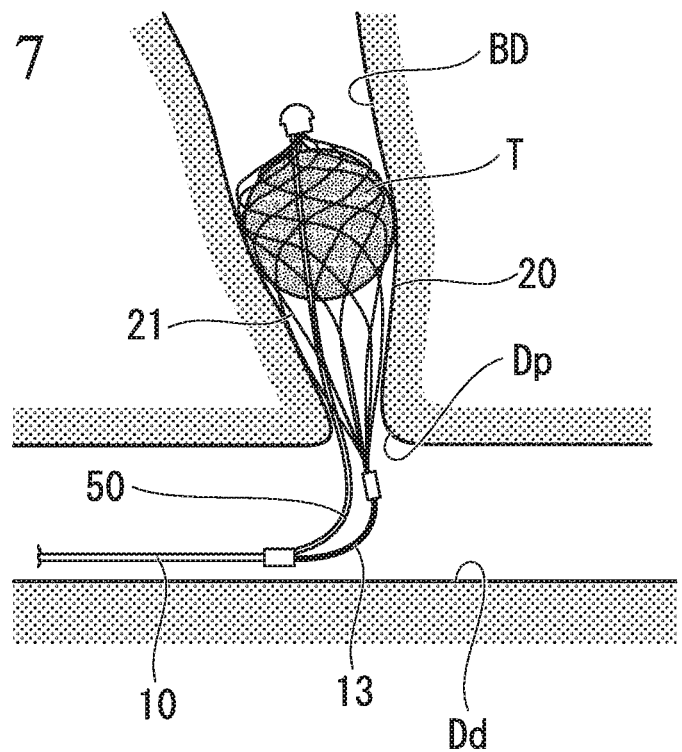
FIG. 7 is a view showing the aspect of using the endoscopic treatment tool according to the first embodiment of the present invention.

Through the steps of a procedure described above, the calculus T is eliminated from the bile duct BD. However, for example, as shown in FIG. 7, in a case where the calculus T greater than the opening of a duodenal papilla Dp is accommodated in the basket part 20, the incarceration occurs in the treatment tool 1 inside the bile duct BD, and the basket part 20 cannot be taken into the duodenum Dd side. In such a case, treatment using a calculus crushing apparatus disclosed in Patent Document 2 is performed.

First, in a case where the incarceration occurs, the operator cuts the sheath 60 and the operating wire 10 at a position in the vicinity of the operating part 70 (position indicated with the arrow A in FIG. 5) and removes the endoscope insertion part 101 and the sheath 60 from the inside of the body. When the endoscope insertion part 101 and the sheath 60 are removed, as shown in FIG. 7, the operating wire 10 and the support member 50 are exposed inside the duodenum Dd. In this case, in a treatment tool in the related art, a proximal end portion of a support member is not connected to an operating wire. Therefore, due to the rigidity of itself, the support member extends in a substantially linear manner independently from bending of the operating wire. Meanwhile, in the present embodiment, since the proximal end portion 51 of the support member 50 is connected along the second operating wire part 13 through the connecting member 80, the support member 50 is bent while following the bending of the second operating wire part 13.

Figure 8:
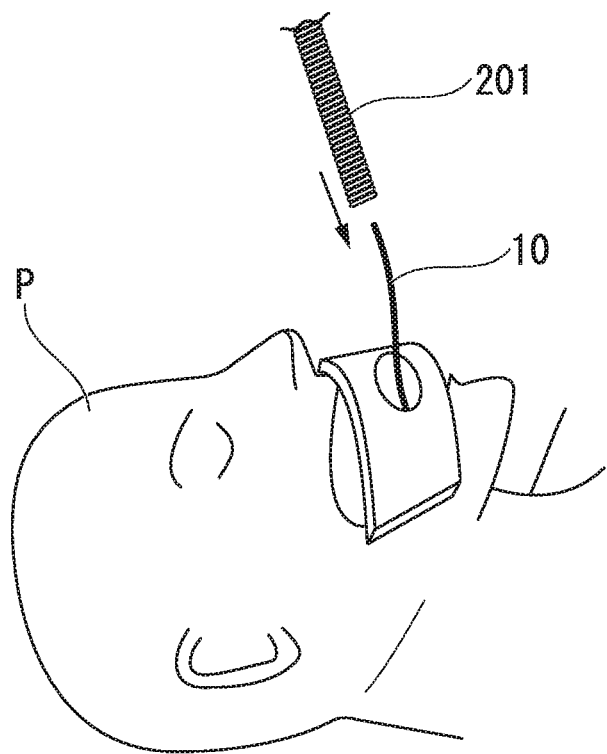
FIG. 8 is a view showing the aspect of using the endoscopic treatment tool according to the first embodiment of the present invention.
Figure 9:
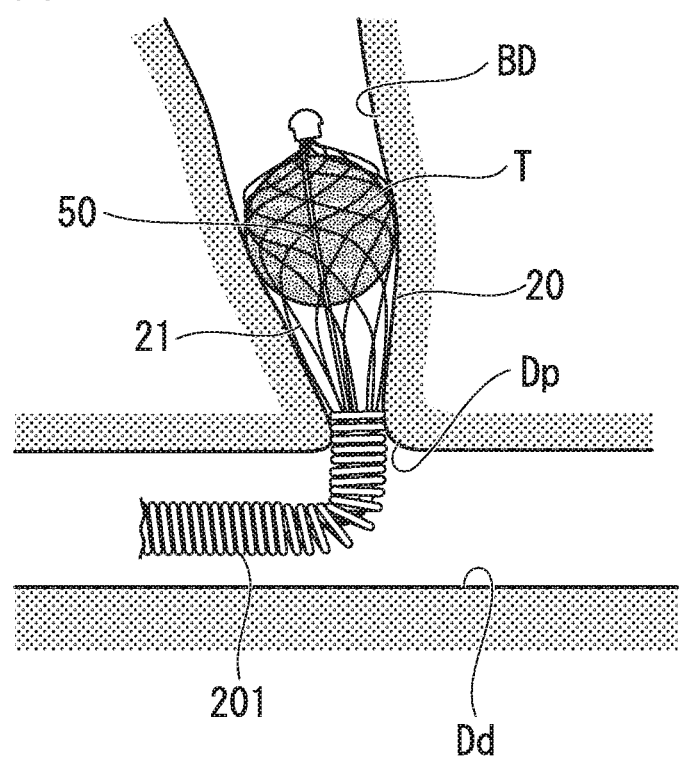
FIG. 9 is a view showing the aspect of using the endoscopic treatment tool according to the first embodiment of the present invention.

As shown in FIG. 8, an operator inserts a portion the proximal side of the cut operating wire 10, the portion bulging out of the mouth of a patient P, into a coil sheath 201 of a calculus crushing apparatus 200 and inserts the coil sheath 201 into the body. The coil sheath 201 is inserted to reach the duodenum Dd and the duodenal papilla Dp along the operating wire 10 and is inserted until the coil sheath 201 reaches at the basket part 20, as shown in FIG. 9.

Figure 10:
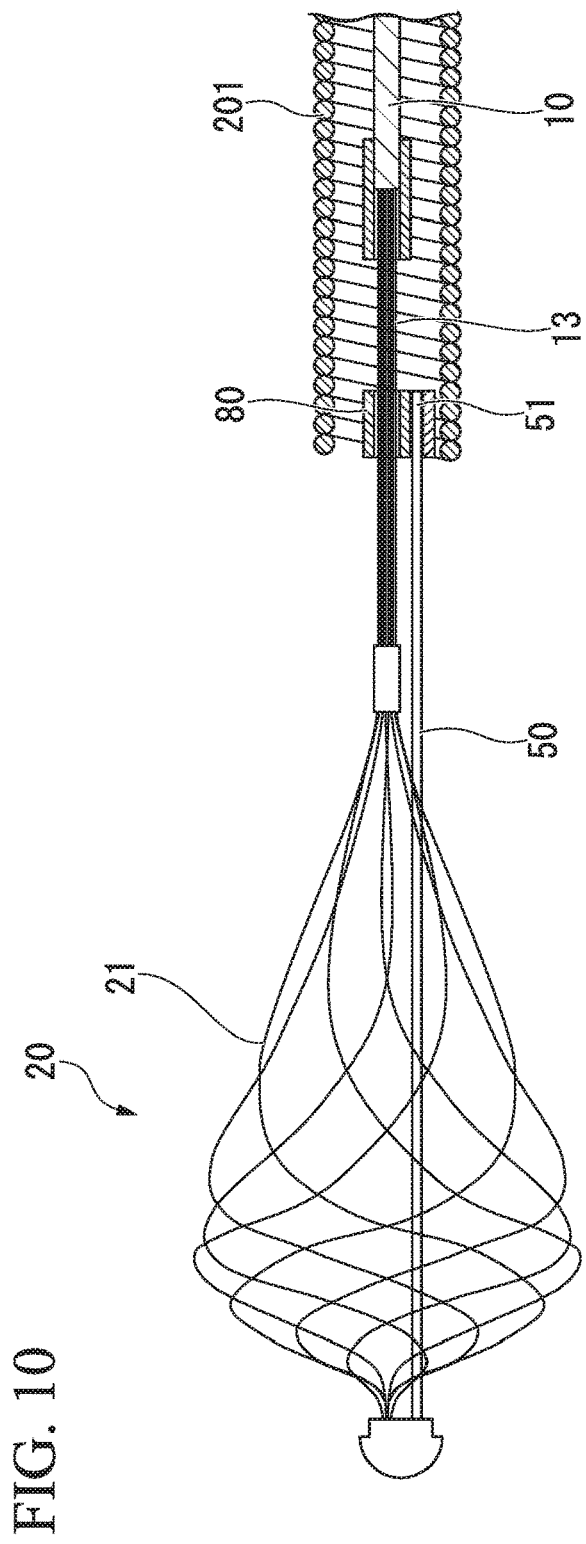
FIG. 10 is a partial cross-sectional view showing the aspect of using the endoscopic treatment tool according to the first embodiment of the present invention.

In this case, the proximal end portion 51 of the support member 50 is connected along the second operating wire part 13 through the connecting member 80. Therefore, as shown in FIG. 10, the operator can smoothly insert the proximal end portion 51 of the support member 50 into the coil sheath 201 together with the second operating wire part 13.

Figure 11:
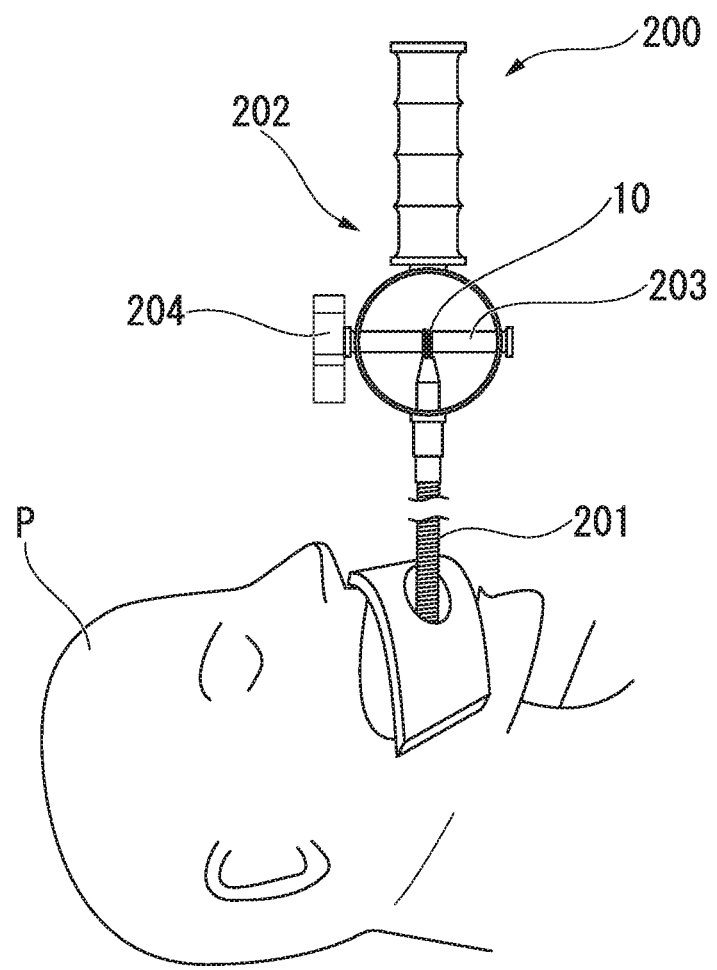
FIG. 11 is a view showing the aspect of using the endoscopic treatment tool according to the first embodiment of the present invention.

Subsequently, as shown in FIG. 11, the operator inserts the proximal end portion of the cut operating wire 10 into an insertion hole (not shown) of a winding shaft 203 of an operating part 202 of the calculus crushing apparatus 200. Thereafter, the winding shaft 203 is rotated by a rotating operation of a handle 204, and the operating wire 10 is wound. As a result, the operating wire 10 is pulled toward the proximal side, a force of being pulled into the coil sheath 201 acts on the basket part 20, and thus, the calculus T is in a state of being sandwiched in the basket part 20. When the operating wire 10 is further wound, the calculus T is tightened and crushed by the plurality of basket wires 21. When the calculus T is crushed, the incarceration is cancelled. Accordingly, the coil sheath 201 and the cut treatment tool 1 are removed to the outside of the body.

In the treatment tool 1 according to the present embodiment, the proximal end portion 51 of the support member 50 is connected to the operating wire 10 in a state where the proximal end portion 51 of the support member 50 is relatively movable with respect to the second operating wire part 13. As a result, during normal use, the support member 50 carries out the original function of supporting the basket part 20. In a case where the incarceration occurs, even after the cut sheath 60 is removed, the proximal end portion 51 of the support member 50 is disposed along the second operating wire part 13. Therefore, the support member 50 is smoothly inserted into the coil sheath 201 of the calculus crushing apparatus 200, and thus, emergency crushing treatment for the calculus T is promptly performed.

The present embodiment shows an example in which on the proximal end side of the basket wires 21, the straight parts 24 are provided on the proximal side than the binding part 40 and a bundle of the straight parts 24 functions as the second operating wire part 13. However, the embodiment may have a configuration in which the binding part and the operating wire are directly connected to each other. In this case, the connecting member 80 is configured that the operating wire 10 is inserted into the through hole 82 on the proximal side than the binding part, and the connecting member 80 and the proximal end portion 51 of the support member 50 relatively move in the longitudinal direction with respect to the operating wire 10 in accordance with a shape change of the basket part 20.

The basket part of the present invention is not limited to the shape shown in the embodiment described above. The basket part may be adopted as long as the basket part being configured with a plurality of basket wires and having a basket shape in which a foreign substance is capable of collecting.

The connecting member of the present embodiment is not limited to the aspect described above. The connecting member may be adopted as long as the proximal end part of the support member 50 is connected to the operating wire 10 such that the support member 50 relatively moves in the longitudinal direction with respect to the operating wire 10. For example, a configuration that the connecting member may be fixed at a predetermined position on the operating wire 10 side in accordance with the length of the support member 50, and the support member 50 is relatively move with respect to the connecting member may be acceptable. Furthermore, for example, the following configurations shown in FIGS. 12 to 23 may use as the connecting member.

(First Modified Example of Connecting Member)

Figure 12:
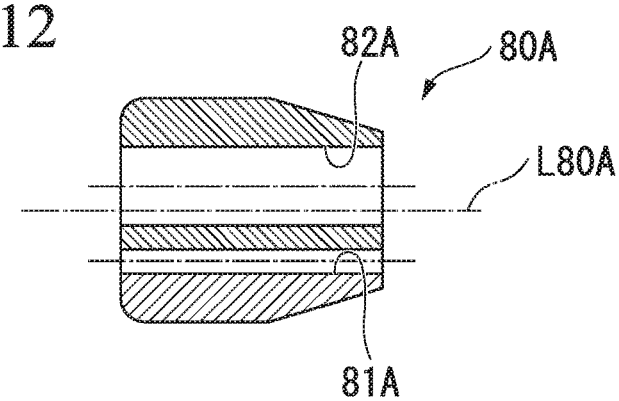
FIG. 12 is a cross-sectional view showing a connecting member in a first modified example of the first embodiment of the present invention.
Figure 13:
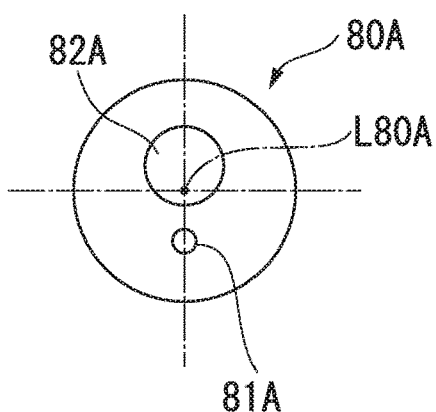
FIG. 13 is a view showing the connecting member in the first modified example of the first embodiment of the present invention when viewed in an axis direction.

FIGS. 12 and 13 are views showing a first modified example of the connecting member. As shown in FIGS. 12 and 13, in a connecting member 80A of the present modified example, an insertion hole 81A and a through hole 82A individually extend and are parallel to a central axis L80A of the connecting member 80A and are formed near the central axis L80A. Due to such a configuration, the second operating wire part 13 (operating wire 10) and the proximal end part of the support member 50 are disposed in the vicinity of the central axis L60 inside the sheath 60 and have a sufficient gap in the sheath 60 with respect to a lumen, and thus, the operating wire 10 can smoothly advance and retract with respect to the sheath 60. A curved face is formed in the circumferential end part of the connecting member 80A on the distal end side, and the connecting member 80A is formed so as to smoothly advance and retract inside the lumen of the sheath 60.

In addition, the connecting member 80A of the present modified example is different from the connecting member 80 of the first embodiment in that the outer diameter of the proximal end side is formed and is smaller than the outer diameter of the distal end side. The connecting member 80A is configured such that the outer diameter on the proximal end side becomes small while ensuring a length required to stably maintain a state where the second operating wire part 13 (operating wire 10) and the proximal end portion 51 of the support member 50 are parallel to each other.

In the connecting member 80A of the present modified example, similar to the connecting member 80 of the first embodiment, while the support member 50 and the operating wire 10 are maintained and are parallel to each other in a state where the proximal end portion 51 of the support member 50 is positioned along a longitudinal axis of the operating wire 10, the proximal end portion 51 of the support member 50 can be connected and is able to relatively move in the axis direction with respect to the operating wire 10. Moreover, the connecting member 80A restrains sliding friction of the sheath 60 with respect to the lumen, and the operating wire 10 can be operated so as to smoothly advance and retract with respect to the sheath 60. In addition, even in a case where incarceration occurs and the connecting member 80A is inserted into the coil sheath 201, the connecting member 80A can be smoothly inserted while restraining sliding friction inside the coil sheath 201.

(Second Modified Example of Connecting Member)

Figure 14:
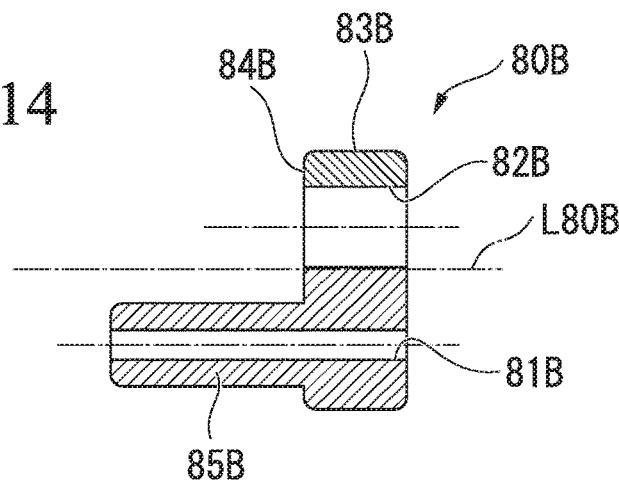
FIG. 14 is a cross-sectional view showing a connecting member in the second modified example of the first embodiment of the present invention.
Figure 15:
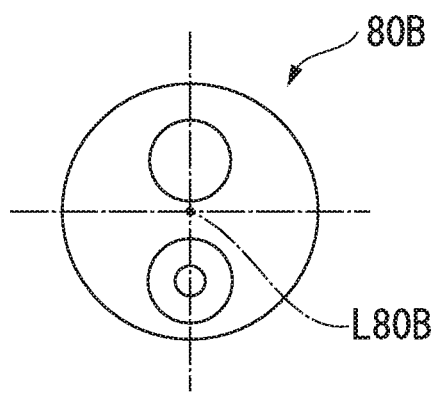
FIG. 15 is a view showing the connecting member in the second modified example of the first embodiment of the present invention when viewed in the axis direction.
Figure 16:
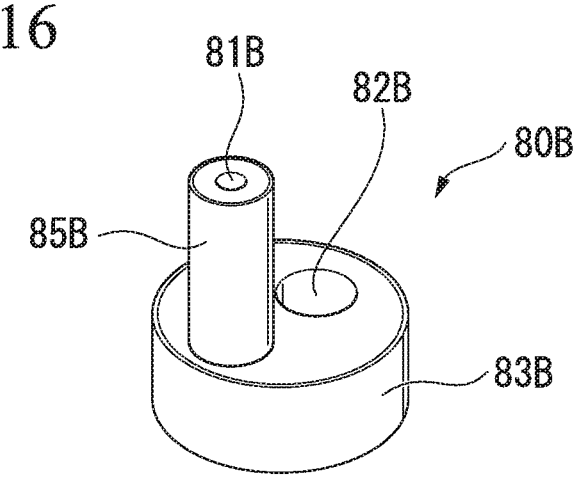
FIG. 16 is a perspective view showing the connecting member in the second modified example of the first embodiment of the present invention.

FIGS. 14 to 16 are views showing a second modified example of the connecting member. As shown in FIGS. 14 and 16, a connecting member 80B of the present modified example is different from the connecting member 80 of the first embodiment in that there are provided a substantially columnar body part (holding part) 83B and an insertion tube 85B which protrudes in a direction of a central axis L80B from a distal end face 84B of the body part 83B. The body part 83B and the insertion tube 85B are integrally molded. As shown in FIG. 15, in the body part 83B, an insertion hole 81B and a through hole 82B extend and are individually parallel to the central axis L80B of the connecting member 80B and are formed near the central axis L80B. The through hole 82B has an opening diameter of a size to the extent that the second operating wire part 13 can advance and retract, and the second operating wire part 13 is inserted therethrough. The insertion hole 81B is formed so as to communicate with the body part 83B and the insertion tube 85B. The insertion hole 81B has an opening diameter such that the proximal end portion 51 of the support member 50 can be inserted and fixed. Due to such a configuration, the second operating wire part 13 (operating wire 10) and the proximal end portion of the support member are disposed in the vicinity of the central axis L60 inside the sheath 60, and the sheath 60 has a sufficient gap with respect to the lumen. Therefore, the operating wire 10 can smoothly advance and retract with respect to the sheath 60.

Moreover, the curved faces are formed in the circumferential end parts of the body part 83B and the insertion tube 85B. The body part 83B and the insertion tube 85B are formed and are smoothly inserted through inside the lumen of the sheath 60.

In the connecting member 80B of the present modified example, similar to the connecting member 80 of the first embodiment, while the support member 50 and the operating wire are maintained and is parallel to each other in a state where the proximal end portion 51 of the support member 50 is positioned along the operating wire 10, the proximal end portion 51 of the support member 50 can be connected and is able to relatively move in the axis direction with respect to the operating wire 10. Moreover, in the connecting member 80B of the present modified example, since the length of a portion in a direction of the central axis L80B in the through hole 82B through which the operating wire 10 is inserted and is able to advance and retract is set to be small, frictional resistance can be reduced by decreasing the contact area between the operating wire 10 and the through hole 82B. Therefore, the connecting member 80B can be prevented from hindering an advance-retract operation of the operating wire 10 with respect to the sheath 60. Moreover, the insertion hole 81B fixing the support member 50 is formed in the body part 83B and the insertion tube 85B, thereby ensuring a length required to stably maintain a state where the operating wire 10 and the proximal end portion 51 of the support member 50 are parallel to each other. Since the outer diameter of the insertion tube 85B is smaller than the outer diameter of the body part 83B, a sufficient gap is ensured between the insertion tube 85B and the lumen of the sheath 60. Therefore, the connecting member 80B can be prevented from hindering an advance-retract operation of the operating wire 10 with respect to the sheath 60.

(Third Modified Example of Connecting Member)

Figure 17:
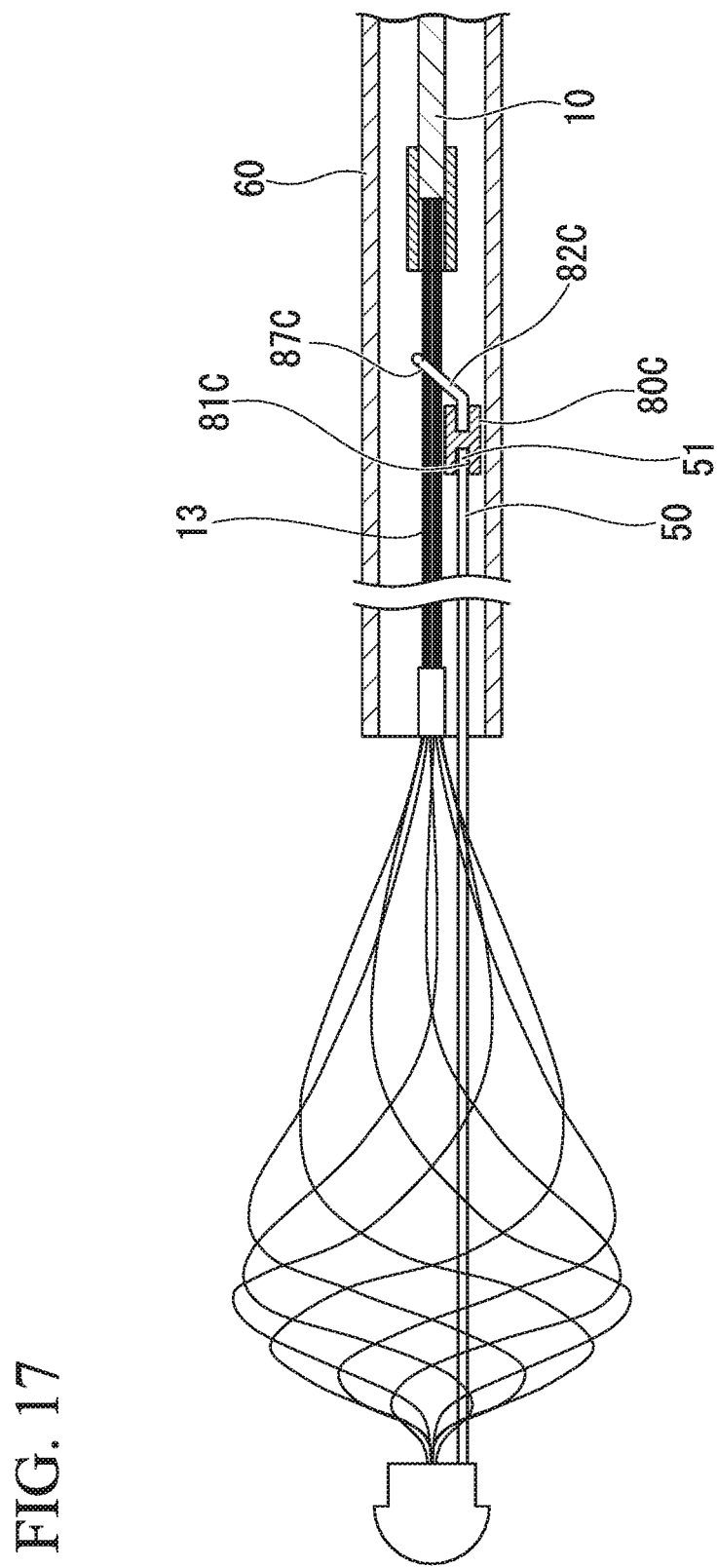
FIG. 17 is a partial cross-sectional view showing the distal end portion of the endoscopic treatment tool provided with the connecting member in the third modified example of the first embodiment of the present invention.
Figure 18:
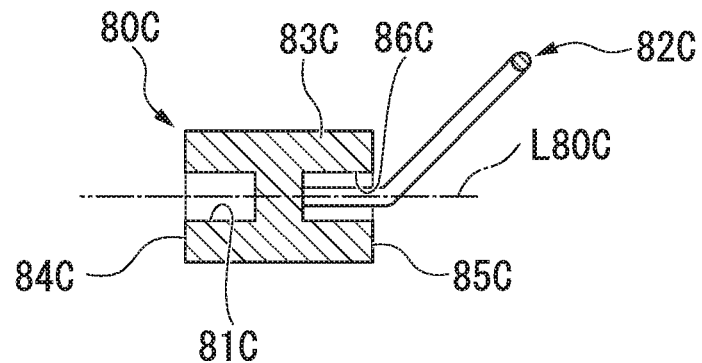
FIG. 18 is a cross-sectional view showing the connecting member in the third modified example of the first embodiment of the present invention.
Figure 19:
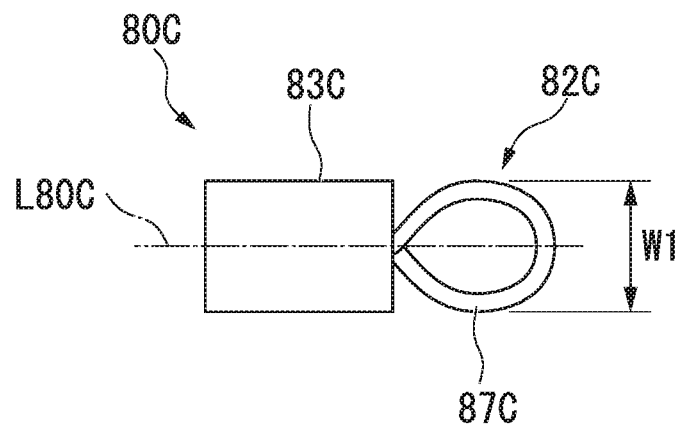
FIG. 19 is a front view showing the connecting member in the third modified example of the first embodiment of the present invention.

FIGS. 17 to 19 are views showing a third modified example of the connecting member. A connecting member 80C of the present modified example is different from that of the first embodiment in regard to a configuration of the insertion hole through which the operating wire 10 is inserted. The connecting member 80C has a substantially columnar body part (holding part) 83C and an insertion ring 82C which is fixed to the body part 83C. The body part 83C has a first insertion hole 81C which is open on a distal end face 84C and is formed on a central axis L80C of the body part 83C, and a second insertion hole 86C which is open on a proximal end face 85C and is formed coaxially with the first insertion hole 81C. The proximal end portion 51 of the support member 50 is inserted into and fixed to the first insertion hole 81C. As shown in FIG. 18, the insertion ring 82C is configured that a loop part (sliding part) 87C is formed of a linear member and the loop part 87C is bent to tilt with respect to the end part. In the insertion ring 82C, the end part formed of a linear member is inserted through the second insertion hole 86C and is fixed, thereby being fixed to the body part 83C. As shown in FIGS. 18 and 19, the loop part 87C of the insertion ring 82C extends outward from the outer circumference of the body part 83C when viewed in a direction orthogonal to the central axis L80C, and the loop is disposed and is opened in a direction of the central axis L80C. As shown in FIG. 17, the support member 50 and the operating wire 10 are connected to each other by inserting the second operating wire part 13 through the loop part 87C of the insertion ring 82C.

In the connecting member 80C, similar to the connecting member 80 of the first embodiment, while the support member 50 and the operating wire 10 are maintained and are parallel to each other in a state where the proximal end portion 51 of the support member 50 is positioned along the operating wire 10, the proximal end portion 51 of the support member 50 can be connected and is able to relatively move in the axis direction with respect to the operating wire 10. Moreover, since the second operating wire part 13 is inserted through the inside of the loop part 87C of the insertion ring 82C formed of a linear member, frictional resistance can be restrained low by restraining the contact area between the loop part 87C and the second operating wire part 13. Moreover, since a sufficient gap is ensured between the insertion ring 82C and the lumen of the sheath 60, the connecting member 80C can be prevented from hindering an advance-retract operation of the operating wire 10 with respect to the sheath 60.

(Fourth Modified Example of Connecting Member)

Figure 20:
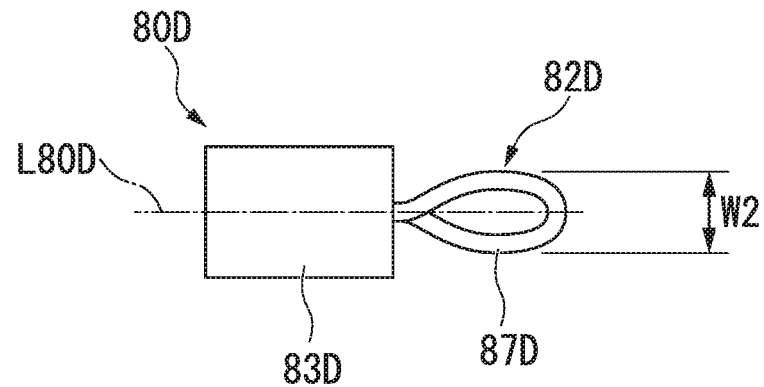
FIG. 20 is a front view showing a connecting member in a fourth modified example of the first embodiment of the present invention.

FIG. 20 is a view showing a fourth modified example of the connecting member. A connecting member 80D of the present modified example is different from the connecting member 80C of the third modified example in regard to the shape of the loop part. In a loop part (sliding part) 87D, a width W2 in a direction orthogonal to a central axis L80D is smaller than a width W1 of the loop part 87C of the connecting member 80C in the third modified example. The width W1 of the loop part 87C of the third modified example has a size substantially equal to the diameter of the body part (holding part) 83C. In contrast, the width W2 of the loop part 87D in the present modification is smaller than the diameter of a body part 83D.

In the connecting member 80D, similar to the connecting member 80 of the first embodiment, while the support member 50 and the operating wire 10 are maintained and are parallel to each other in a state where the proximal end portion 51 of the support member 50 is positioned along the operating wire 10, the proximal end portion 51 of the support member 50 can be connected and is able to relatively move in the axis direction with respect to the operating wire 10. Moreover, similar to the connecting member 80C of the third modified example, frictional resistance can be restrained low by restraining the contact area between the loop part 87D and the second operating wire part 13. Moreover, since a sufficient gap is ensured between an insertion ring 82D and the lumen of the sheath 60, the connecting member 80D can be prevented from hindering an advance-retract operation of the operating wire 10 with respect to the sheath 60.

(Fifth Modified Example of Connecting Member)

Figure 21:
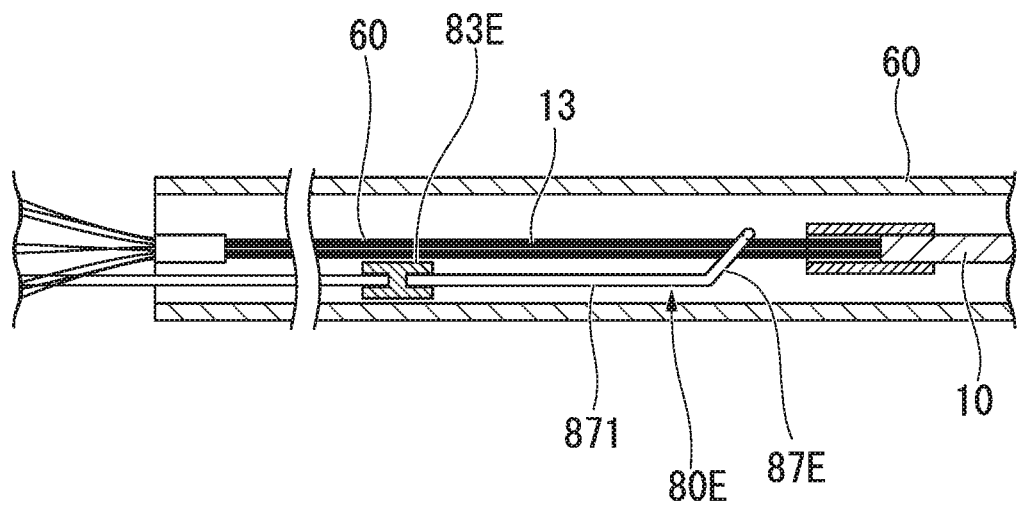
FIG. 21 is a cross-sectional view showing a connecting member in a fifth modified example of the first embodiment of the present invention.
Figure 22:
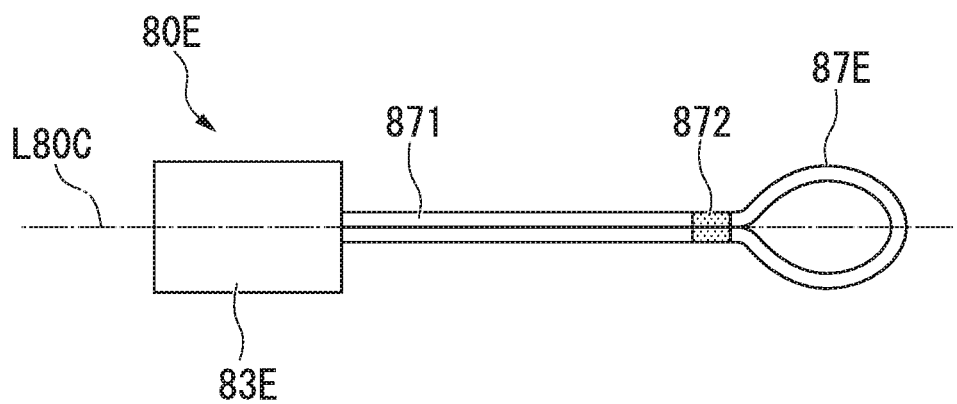
FIG. 22 is a front view showing the connecting member in the fifth modified example of the first embodiment of the present invention.

FIG. 21 is a view showing a fifth modified example of the connecting member. A connecting member 80E of the present modified example is different from the connecting member 80C of the third modified example in regard to the shape of the connecting portion between a loop part 87E and a body part 83E. Between the loop part (sliding part) 87E and the body part 83E, a linear portion 871 having a predetermined length (for example, 20 mm) is provided, thereby having a configuration having a uniform distance between the loop part 87E and the body part 83E. The length of the linear portion 871 is favorably set such that the distance between the loop part 87E and the body part 83E is lengthened within a range in which sliding of the loop part 87E and the basket part 20 is not influenced. In the present modified example, the length of the linear portion 871 is set to be longer than the lengths of the loop part 87E and the body part 83E. In the loop part 87E and the linear portion 871, as shown in FIG. 22, a loop having a large diameter is formed in an intermediate portion of the wire, and the loop part 87E and the linear portion 871 are formed by fixing at least a portion 872 of the wire of the linear portion 871 through brazing or by using an adhesive or the like.

Figure 23:
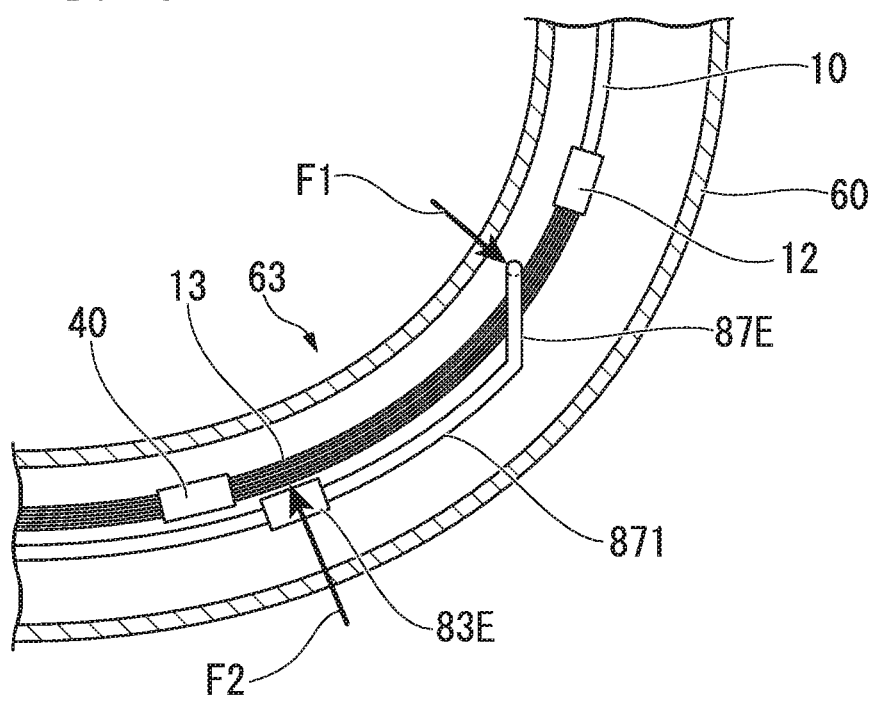
FIG. 23 is a view showing an aspect of using the connecting member in the fifth modified example of the first embodiment of the present invention.

Generally, when the operating wire is pulled in a state where the sheath 60 in the vicinity of the position of the connecting member is bent, as shown in FIG. 23, on a hand side of the bending part of the sheath 60, the basket wires 21 lean inward with respect to the bending of the sheath 60. On the other hand, a force tending to return to the central axis side of the sheath 60 acts on the loop part. Due to this action, the basket wires 21 receive a force in an arrow F1 direction from the loop part 87E. In addition, on the distal end side of a sheath bending part, the basket wires 21 lean in an outward direction with respect to the bending of the sheath 60. On the other hand, the body part 83E tends to return to the central axis side of the sheath 60. Due to this action, a force in an arrow F2 direction opposite to the arrow F1 direction is applied to the basket wires 21 from the body part. Here, when the distance between the loop part 87E and the body part 83E is short, the distance between two points, that is, a point to which a force in the F1 direction is applied and a point to which a force in the F2 direction is applied becomes short. Therefore, the basket wires are unlikely to release the forces, and there is a possibility that the sliding friction of the basket wires increases.

In the present modified example, the distance between the loop part 87E and the body part 83E is configured to have a predetermined length. Therefore, as shown in FIG. 23, the distance between the point to which a force in the F1 direction is applied and the point to which a force in the F2 direction is applied also becomes lengthened. Accordingly, the deformable amount of the basket wires between two points becomes significant, and the forces are likely to be released. As a result, even in a state where the sheath 60 is bent, sliding friction of the basket wire 21 is prevented from increasing, and thus, an operation can be smoothly performed.

Second Embodiment

Figure 24:
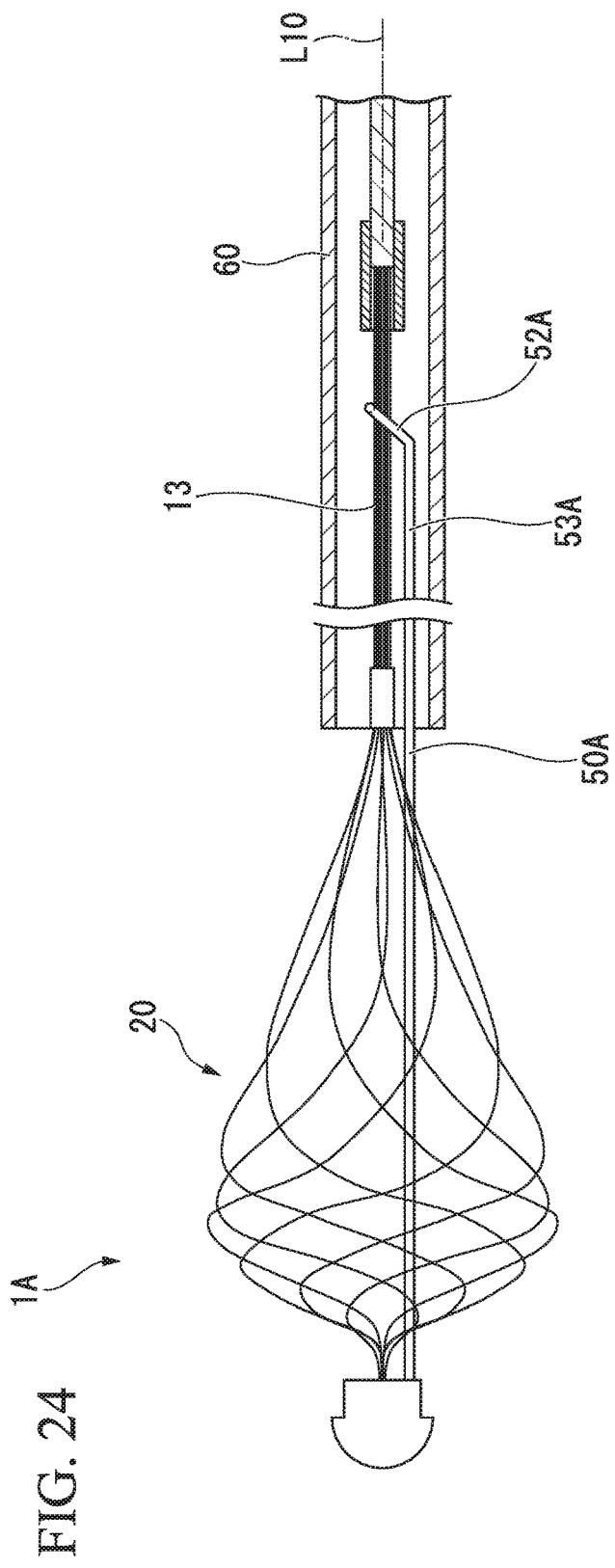
FIG. 24 is a cross-sectional view showing a distal end portion of an endoscopic treatment tool according to a second embodiment of the present invention.
Figure 25:
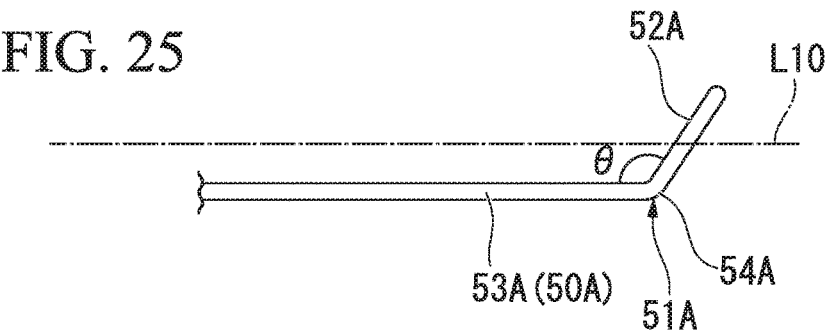
FIG. 25 is a side view showing a connecting member of the endoscopic treatment tool according to the second embodiment of the present invention.
Figure 26:
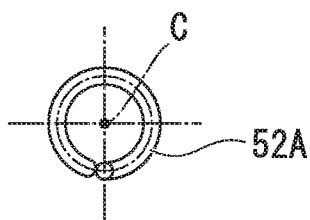
FIG. 26 is a view showing the connecting member of the endoscopic treatment tool according to the second embodiment of the present invention when viewed in the axis direction.
Figure 27:
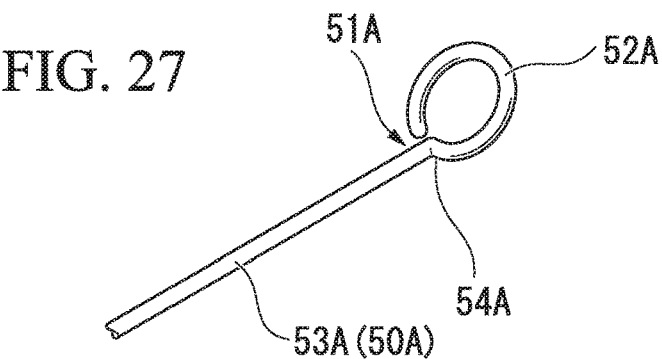
FIG. 27 is a perspective view showing the connecting member of the endoscopic treatment tool according to the second embodiment of the present invention.

A treatment tool 1A according to a second embodiment will be described with reference to FIGS. 24 to 27. The present embodiment is different from the first embodiment in regard to the connection structure of the support member and the operating wire. In the following description, the same reference signs will be applied to common configurations and the like which have already been described, and overlapping description will be omitted. FIG. 24 is a partial cross-sectional view showing the distal end portion of the treatment tool 1A. FIG. 25 is a side view of a proximal end portion 51A of a support member 50A of the present embodiment. FIG. 26 is a view when the support member 50A of the present embodiment is viewed from the distal end portion side. FIG. 27 is a perspective view of the proximal end portion 51A of the support member 50A of the present embodiment.

In place of the connecting member 80 of the first embodiment, the treatment tool 1A of the present embodiment has a loop part (sliding part) 52A in the proximal end portion 51A of the support member 50A. That is, as shown in FIG. 27, in the support member 50A, the loop part 52A wound with one round at the proximal end portion 51A is formed, and the loop part 52A functions as an insertion path of the operating wire 10. A bent part 54A is provided between a straight part 53A of the support member 50A and the loop part 52A. As shown in FIG. 25, the loop part 52A is disposed so as to tilt with respect to the support member 50A when viewed in a direction orthogonal to the axis direction. As shown in FIG. 26, in the loop part 52A, in a state where the operating wire is inserted therethrough, a center C of the loop part 52A is formed so as to substantially coincide with the central axis L10 of the operating wire 10.

In a viewpoint in which the operating wire 10 is inserted through the loop part 52A and is able to advance and retract, an angle θ of the bent part 54A may be a right angle. However, when the angle θ of the bent part 54A is an obtuse angle, the size of the proximal end portion 51A of the support member 50A in a direction orthogonal to the axis can be reduced. Moreover, the entire diameter of the support member 50A through which the operating wire 10 is inserted and the operating wire 10 can be restrained small. Therefore, when the angle θ of the bent part 54A is an obtuse angle, the support member 50A and the operating wire 10 can smoothly move inside the sheath 60.

Figure 28:
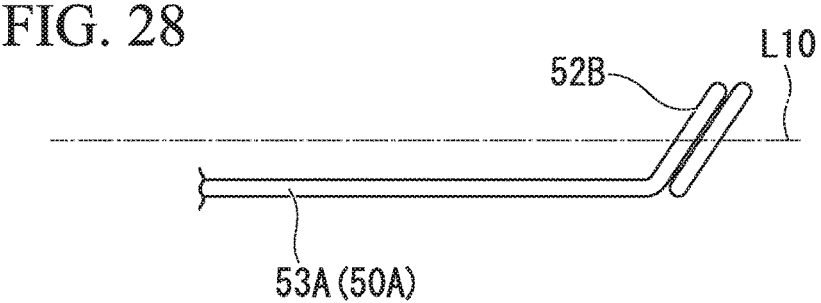
FIG. 28 is a side view showing a connecting member of in a modified example of the second embodiment of the present invention.

The loop part 52A is not limited to the form described above as long as the operating wire 10 can be inserted through. For example, as shown in FIG. 28, a loop part (sliding part) 52B may be configured to be wound with multiple rounds (in the example shown in FIG. 28, two rounds). The bent shape of the loop part is not also limited to the circular shape.

According to the present embodiment, similar to the embodiment described above, while the support member 50 and the operating wire 10 are maintained and are parallel to each other in a state where the proximal end portion 51 of the support member 50 is positioned along the operating wire, the proximal end portion 51 of the support member 50 can be connected and is able to relatively move in the axis direction with respect to the operating wire 10. Moreover, in the treatment tool 1A of the present embodiment, the support member 50 and the operating wire 10 can be connected to each other through a simple configuration in which the loop part 52A is formed in the proximal end portion 51A of the support member 50A.

Hereinbefore, the embodiments of the present invention have been described in detail with reference to the drawings. However, the specific configurations are not limited to the embodiments, and the embodiments also include a design change and the like within a range without departing from the gist of the present invention.

In addition, the configuration elements shown in each of the embodiments and each of the modified examples described above can be configured by suitably combining together.

What is claimed is:

1. An endoscopic treatment tool comprising:
a sheath;
an operating wire inserted into the sheath and being configured to advance and retract;
a basket part positioned at a distal side of the operating wire and formed by binding a plurality of elastic basket wires having helical shapes in a natural state;
a distal end tip which binds and fixes distal ends of the plurality of basket wires at a distal end of the basket part;
a binding part in which proximal end portions of the plurality of basket wires are bound together and fixed; and
a support member disposed through the basket part along a central axis of the basket part, a proximal end portion of the support member being positioned inside the sheath, and a distal end portion of the support member being fixed to the distal end tip; and
a connecting member positioned more proximally than the binding part, the connecting member including an insertion hole, the support member being configured to be inserted into the insertion hole to connect the proximal end portion of the support member to the operating wire inside the sheath, the proximal end portion of the support member being provided along a longitudinal axis of the operating wire.

2. The endoscopic treatment tool according to claim 1, wherein the binding part and a connecting part between the distal end tip and the distal ends of the plurality of basket wires are positioned on the central axis, and wherein the support member is disposed at a position offset radially outward with respect to the central axis.

3. The endoscopic treatment tool according to claim 2, wherein the connecting member includes a sliding part configured to slide with respect to the operating wire, and a holding part holding the proximal end portion of the support member at the position offset from the sliding part and along the central axis.

4. The endoscopic treatment tool according to claim 3, wherein:
the connecting member is formed of a pipe-shaped member; and
a through hole through which the operating wire is inserted and the insertion hole through which the support member is inserted are formed side by side in the central axis direction.

5. The endoscopic treatment tool according to claim 3, wherein the connecting member has a loop part which is provided at a position extending from a proximal end of the support member and through which the operating wire is inserted.

6. The endoscopic treatment tool according to claim 1, wherein the connecting member is configured to move with respect to the sheath along the central axis.

7. The endoscopic treatment tool according to claim 1, wherein:
the connecting member is fixed to the proximal end portion of the supporting member or the operating wire; and
one of the proximal end portion of the supporting member and the operating wire is connected to the connecting member and is configured to slide in the sheath along the central axis and to slide with respect to the other one of the proximal end portion of the supporting member and the operating wire.

8. The endoscopic treatment tool according to claim 1, wherein the connecting member is fixed to the proximal end portion of the supporting member, and is connected to the operating wire such that the connecting member is configured to slide along the central axis with respect to the operating wire.

9. An endoscopic treatment tool comprising:
a sheath;
an operating wire inserted into the sheath and being configured to advance and retract;
a basket part positioned at a distal side of the operating wire and formed by binding a plurality of elastic basket wires having helical shapes in a natural state;
a distal end tip which binds and fixes distal ends of the plurality of basket wires at a distal end of the basket part;
a binding part in which proximal end portions of the plurality of basket wires are bound together and fixed; and
a support member disposed through the basket part along a central axis of the basket part, a proximal end portion of the support member being positioned inside the sheath, and a distal end portion of the support member being fixed to the distal end tip; and
a connecting member positioned at a proximal side than the binding part, the connecting member connecting the proximal end portion of the support member with the operating wire inside the sheath such that the proximal end portion of the support member is along a longitudinal axis of the operating wherein the connecting member includes:
a sliding part configured to slide with respect to the operating wire; and
a holding part holding the proximal end portion of the support member at the position offset from the sliding part and along the central axis.

10. The endoscopic treatment tool according to claim 9, wherein:
the connecting member is formed of a pipe-shaped member; and
a through hole through which the operating wire is inserted and the insertion hole through which the support member is inserted are formed side by side in the central axis direction.

11. The endoscopic treatment tool according to claim 9, wherein the connecting member has a loop part which is provided at a position extending from a proximal end of the support member and through which the operating wire is inserted.

12. The endoscopic treatment tool according to claim 9, wherein the connecting member is configured to move with respect to the sheath along the central axis.

13. The endoscopic treatment tool according to claim 9, wherein:
the connecting member is fixed to the proximal end portion of the supporting member or the operating wire; and
one of the proximal end portion of the supporting member and the operating wire is connected to the connecting member and is configured to slide in the sheath along the central axis and to slide with respect to the other one of the proximal end portion of the supporting member and the operating wire.

14. The endoscopic treatment tool according to claim 9, wherein the connecting member is fixed to the proximal end portion of the supporting member, and is connected to the operating wire such that the connecting member is configured to slide along the central axis with respect to the operating wire.

15. The endoscopic treatment tool according to claim 9, wherein the binding part and a connecting part between the distal end tip and the distal ends of the plurality of basket wires are positioned on the central axis, and wherein the support member is disposed at a position offset radially outward with respect to the central axis.

\* \* \* \* \*